United States Patent [19]

Kälberer et al.

[11] Patent Number: 5,609,647
[45] Date of Patent: Mar. 11, 1997

[54] SPHERICAL HIP JOINT SOCKET

[75] Inventors: Hartmut Kälberer, Deizisau; Hans-Georg Pfaff, Ostfildern, both of Germany

[73] Assignee: Cerasiv GmbH, Innovatives Keramik-Engineering, Plochingen, Germany

[21] Appl. No.: 324,266

[22] Filed: Oct. 17, 1994

[30] Foreign Application Priority Data

Nov. 6, 1993 [DE] Germany .................. 43 37 936.2

[51] Int. Cl.[6] .................................................. A61F 2/32
[52] U.S. Cl. .................................... 623/22; 623/18
[58] Field of Search ............................ 623/16, 18, 20, 623/22, 23

[56] References Cited

U.S. PATENT DOCUMENTS

| 3,894,297 | 7/1975 | Mittelmeier et al. | 623/22 |
| 4,718,911 | 1/1988 | Kenna | 623/22 |
| 5,080,678 | 1/1992 | Spotorno et al. | 623/22 |

Primary Examiner—Randy C. Shay
Attorney, Agent, or Firm—Felfe & Lynch

[57] ABSTRACT

The invention relates to a hip joint socket for insertion into bone tissue, with an outer metal shell and an inner ceramic shell, the ceramic shell being anchored in the metal shell. To reduce its size while simultaneously reducing the wall thickness of the ceramic shell the inside of the metal shell and the outside of the ceramic shell have a spherical shape accurately fitted to one another and means are disposed for equalizing the transmission of force between the ceramic shell and the metal shell.

12 Claims, 3 Drawing Sheets

SPHERICAL HIP JOINT SOCKET

BACKGROUND OF THE INVENTION

The invention relates to a hip joint socket for insertion into bone tissue and which has an outside metal shell and a ceramic shell anchored in the metal shell.

Hip joint endoprostheses consist of a hip joint socket which is anchored in the pelvic bone, and a ball which is rotatably inserted into the socket and is anchored to a shaft in the femur.

Hip joint sockets consist of an outer metal shell which constitutes the shape of the implant and includes an inner shell that is made of ceramic. The ceramic shell is mechanically anchored in the outer metal shell. There are also inner shells of plastic. The term, metal shell, is synonymous with the metallic part of the acetabular implant, whose outer shape can be configured in accordance with medical requirements.

It is state of the art to fix the inner ceramic shell in the metal shell by means of a taper lock. The angle of the taper lock is 5° 43', i.e., an angle ratio of 1:10.

A disadvantage of this taper lock is that once inserted, a ceramic shell can no longer be removed from the metal shell because the seizing forces are too great. Thus it is difficult to replace the friction bearing component, i.e., the ceramic shell, during a surgical operation or in the case of a re-operation. Usually, the entire socket implant must then be removed or the ceramic inlay destroyed. This, however, leads to problems on account of the formation of splinters.

Another disadvantage of the taper lock is an undesirable load-beating function for the ceramic component. The latter is gripped by the outer taper ring and is then cantilevered on the domed side, resulting in considerable tensile stress on the component. In order to design a socket inlay to deal with the mechanical stresses considerable wall thicknesses (at least 4–5 mm) are necessary. As a result, the ceramic-metal sockets have a large outside diameter. However, from the medical viewpoint, small components are desirable in order to minimize bone loss.

The present invention is addressed to providing an unproved hip joint socket of the type previously described such that it will be of a small size with a thin wall thickness of the ceramic shell.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

FIG. 2b shows a plan view of the face side of metal shell 10 of FIG. 2a;

THE INVENTION

The above stated objects and others are obtained in accordance with the invention by providing a structure wherein the inside of the metal shell and the outside of the ceramic shell have a spherical shape precisely fitted to one another, and means are provided for spreading out the transfer of force between the ceramic shell and the metal shell.

On account of the precisely fitted interior shape of the metal shell and the exterior shape of the ceramic shell, the ceramic shell can have an extremely thin wall, since all the effects of force on the metal shell are equalized. Thus, the size of the implant is extremely small, minimizing the bone mass which must be removed by the surgeon.

Means are disposed in accordance with the invention between the ceramic shell and the metal shell to equalize the transmission of force. Such a structural arrangement compensates for peak stresses which occur due to technically caused and unavoidable dimensional variations.

Two different means are provided for equalizing the transmission of force. In a first embodiment the means is an intermediate layer of plastic, preferably an ultra-high molecular weight plastic, such as for example UHMWPE (ultra high molecular weight polyethylene). This intermediate layer prevents any concentration of stress harmful to the ceramic.

The intermediate layer is expediently surrounded on all sides by the metal shell and the ceramic shell. This prevents any deformation or extrusion through fissures in the intermediate layer.

In an alternative embodiment the means for equalizing the transmission of force is a surface roughening applied to the inside of the metal shell, making the surface plastically deformable. The surface roughening enables the roughened surface of the metal shell to yield and compensate for dimensional inaccuracies.

According to the invention, the surface roughening has a roughness of 4 µm to 100 µm. A roughness of 20 µm to 40 µm is preferred. Advantageously the surface roughening can have an irregular texture produced by, for example, grinding. However, a regular texture of the surface roughening produced by, for example, turning is preferred. In a preferred embodiment the regular texture consists of concentric circles or has a spiral shape formed by a turning operation.

The ceramic shell is anchored in the metal shell by a retaining ring which is fastened on the margin of the metal shell.

Figure 1:
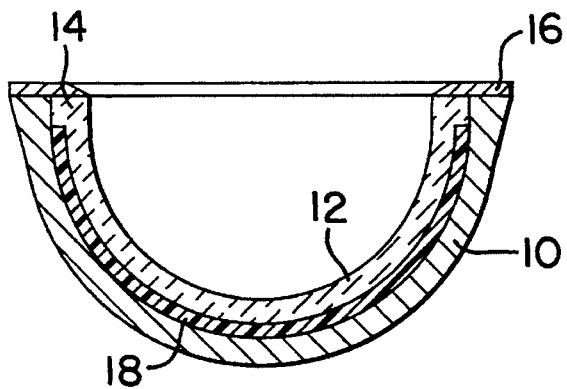
FIG. 1 shows a cross section of a hip joint socket of the invention with a plastic layer between the ceramic shell and the metal shelf.

Referring to the drawings, FIG. 1 shows in cross section a hip joint socket according to the invention, with an outer metal shell 10 which constitutes the outer shape of the implant, and an inner ceramic shell 12. The two shells 10 and 12 have spherical shapes matched to one another. The ceramic shell 12 has on its face side a flange-like collar 14 whose upper margin is at the same level as the upper margin of the metal shell 10. The ceramic shell 12 is locked and anchored in the metal shell 10 by a retaining ring 16. Below the collar 14 is an intermediate layer 18 of plastic between the ceramic shell 12 and the metal shell 10. Intermediate layer 18 completely fills out the space between ceramic shell 12 and metal shell 10. Accordingly, the intermediate layer is defined by the metal shell 10, the ceramic shell 12, and by the collar 14 at the upper end. This intermediate layer of plastic, preferably an ultra-high molecular weight plastic, serves to equalize the transmission of forces from the ceramic shell 12 to the metal shell 10, so that no stress peaks harmful to the ceramic occur. Layer 18 is completely enveloped so that deformation is prevented.

Figure 2A:
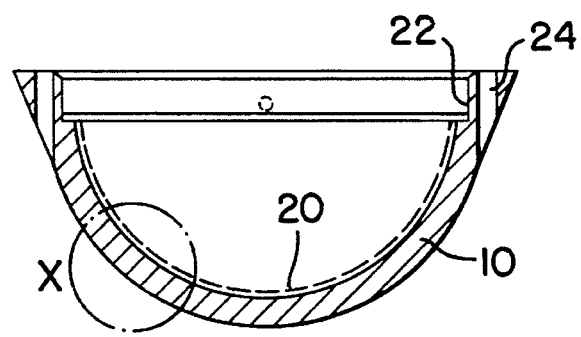
FIG. 2a shows in section a metal shell 10 according to the invention with a surface roughening.
Figure 2B:
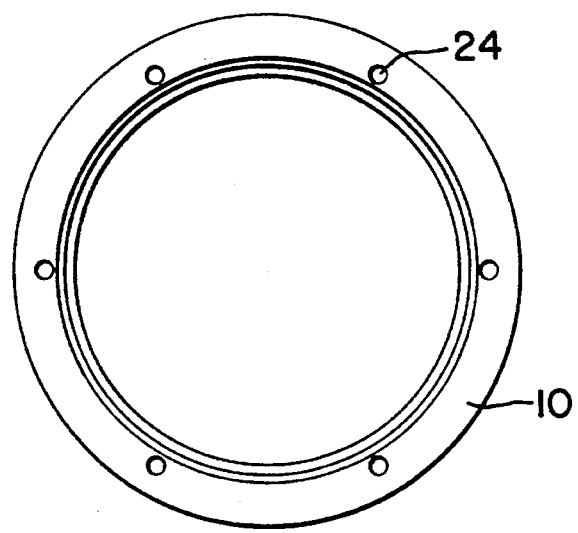

FIG. 2a and b show an alternative embodiment in which, for the equalization of the transmission of forces, no intermediate layer of plastic is provided, but a surface roughening 20 is applied to the inside of the metal shell 10, making the surface plastically deformable. FIG. 2a shows in section a metal shell 10 according to the invention, whose face side has a recess 22 for a collar of a ceramic shell. On the margin of the metal shell 10 bores 24 running lengthwise are disposed, which serve for fastening a retaining ring. FIG. 2b shows a plan view of the face side of the metal shell 10 in FIG. 2a.

The surface roughening 20 has a roughness of 4 μm to 100 μm. A roughness of 20 μm to 40 μm is especially advantageous.

When the ceramic shell is inserted, the surface roughening 20 deforms plastically, so that stress peaks are thereby absorbed.

Figure 3A:
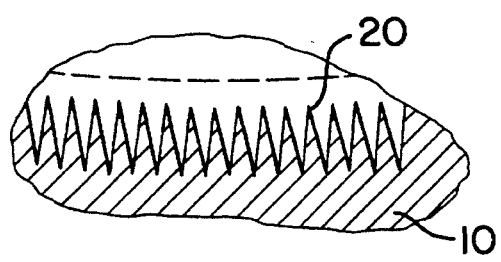
FIG. 3a shows a detail X from FIG. 2a with a sawtooth texture.
Figure 3B:
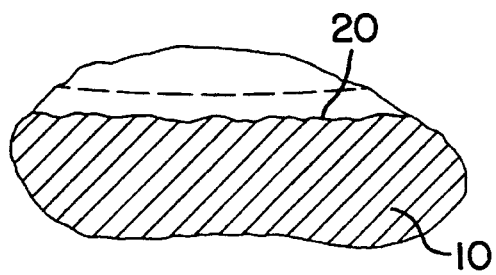
FIG. 3b shows a detail X from FIG. 2a with an irregular texture.

FIG. 3 shows an enlargement of a surface roughening 20 in the form of a sawtooth profile. The surface roughening 20 can be produced by grinding, for example, which produces an irregular texture. The surface roughening 20 can also be applied advantageously by turning, for example, producing a regular texture.

Figure 8:
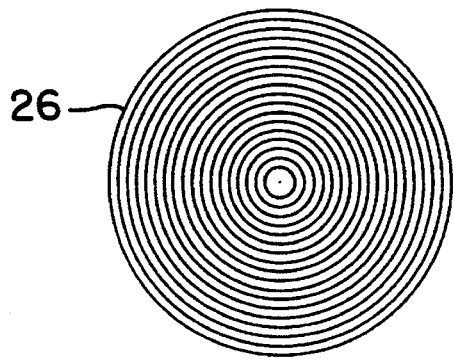
FIG. 8 schematically shows concentric rings applied to the interior surface of the metal shell.
Figure 9:
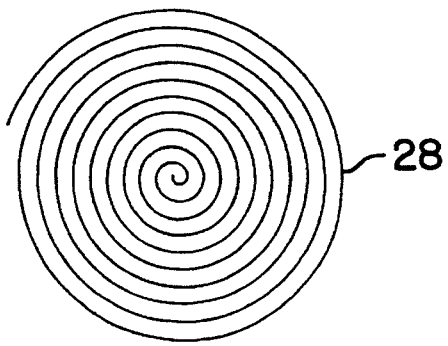
FIG. 9 schematically shows a spiral surface roughening applied to the interior surface of the metal shell.

FIG. 8 shows as preferred embodiment concentric circles 26 as surface roughening. However, other textures are also possible, such as a spiral, for example. Such surface roughening is shown in FIG. 9. The spiral-shaped surface roughening is identified by the reference number 28.

Figure 4:
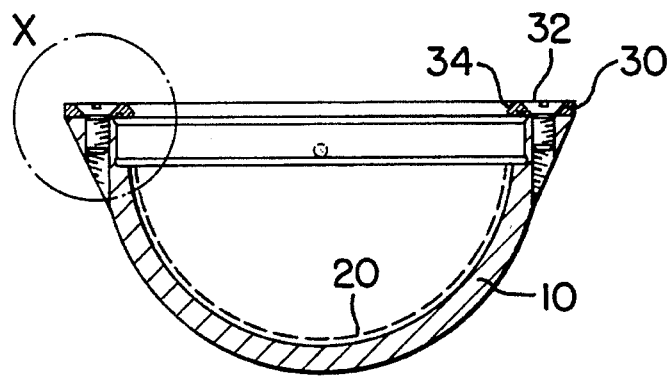
FIG. 4 shows a metal shell of the invention with a retaining ring installed.

In FIG. 4 the metal shell 10 according to the invention is shown with the retaining ring 30 in place. The retaining ring is fastened to the metal shell 10 by screws 32. The screws 32 are driven into the bores 24 already described in FIG. 2a.

Figure 6:
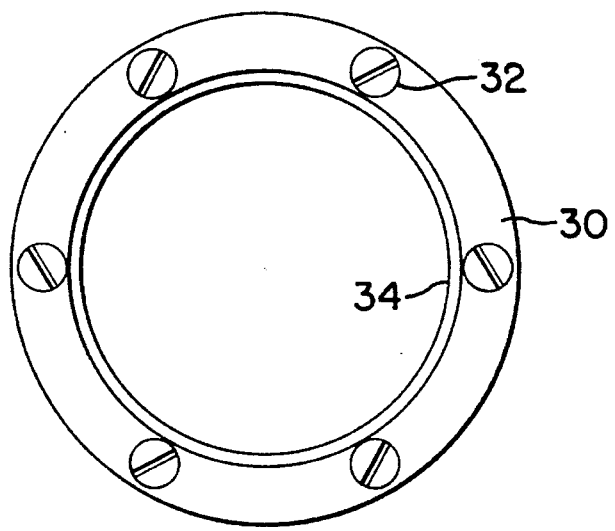
FIG. 6 shows a retaining ring for locking the ceramic shell in the metal shell.

In FIG. 6 the retaining ring 30 is represented with the screws 32 in place. The projection 34 rests on the ceramic ring not shown here and presses it into the metal shell 10.

Figure 5:
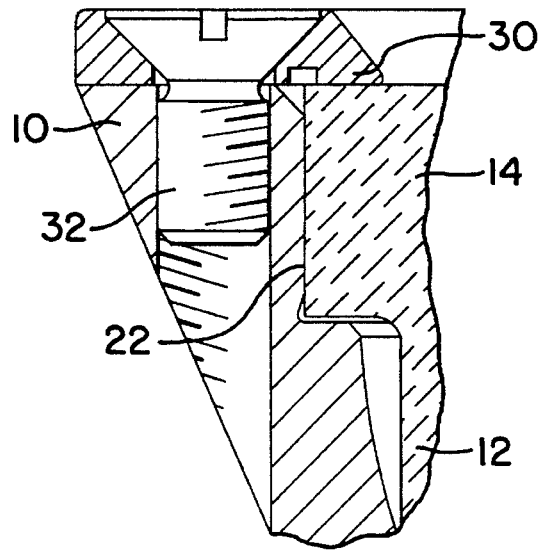
FIG. 5 shows an enlarged detail X from FIG. 4.

FIG. 5 shows an enlargement of the detail X of FIG. 4, with the ceramic shell 12 in place. The ceramic shell 12 rests with its collar 14 in the recess 22 and is pressed into the metal shell 10 by the retaining ring 30. During the pressing the surface roughening 20 of the metal shell 10 deforms plastically.

Figure 7:
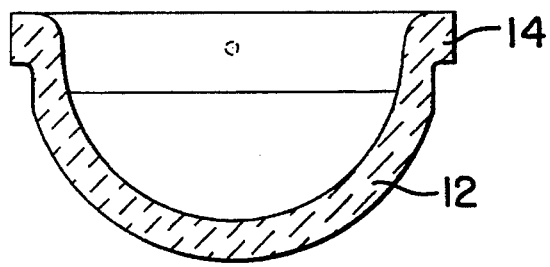
FIG. 7 shows a ceramic shell of the invention in cross section.

FIG. 7 shows the ceramic ring 12 with its collar 14.

The hip joint socket according to the invention is characterized by an extremely small size. Another advantage is that the ceramic shell 12 can be replaced simply by unscrewing the retaining ring 30 even during a surgical operation.

It will be understood that the specification and examples are illustrative but not limitative of the present invention and that other embodiments within the spirit and scope of the invention will suggest themselves to those skilled in the art.

We claim:

1. A hip joint socket for insertion into bone tissue, comprising: a spherically shaped outside metal shell; a spherically shaped ceramic shell anchored in the metal shell wherein the inside of the metal shell and the outside of the ceramic shell are accurately fitted to one another; and means for the equalization of the transmission of forces between the ceramic shell and the metal shell wherein said means comprises a surface roughening applied to the inside surface of the metal shell, whereby the surface is plastically deformable.

2. The hip joint socket of claim 1, wherein the surface roughening has a roughness of 4 μm to 100 μm.

3. The hip joint socket of claim 1, wherein the surface roughening has a roughness of 20 μm to 40 μm.

4. The hip joint socket of claim 1, wherein the surface roughening has an irregular texture.

5. The hip joint socket of claim 1, wherein the surface roughening has a regular texture.

6. The hip joint socket of claim 5, wherein the surface roughening with the regular texture is a turning surface roughening.

7. The hip joint socket of claim 5, wherein the regular texture is in the form of concentric circles.

8. The hip joint socket of claim 5, wherein the regular texture has a spiral shape.

9. The hip joint socket of claim 8, wherein the surface roughening with the regular texture is a turning surface roughening.

10. The hip joint socket of claim 5, wherein the regular texture has a sawtooth arrangement.

11. The hip joint socket of claim 1, wherein the metal shell is formed with a margin.

12. The hip joint socket of claim 11 further comprising a retaining ring fastened on the margin of the metal shell and anchoring the ceramic shell in the metal shell.

* * * * *